United States Patent
Hausladen et al.

(10) Patent No.: US 8,678,645 B2
(45) Date of Patent: Mar. 25, 2014

(54) DEVICE FOR MONITORING THE FLOW OF WATER VAPOR

(75) Inventors: Josef Hausladen, Worth/Donau (DE); Hannelore Sollner, Holzheim Am Forst (DE); Bettina Huber, Regensburg (DE)

(73) Assignee: Krones AG, Neutraubling (DE)

( * ) Notice: Subject to any disclaimer, the term of this patent is extended or adjusted under 35 U.S.C. 154(b) by 865 days.

(21) Appl. No.: 12/564,640

(22) Filed: Sep. 22, 2009

(65) Prior Publication Data
US 2010/0071475 A1    Mar. 25, 2010

(30) Foreign Application Priority Data
Sep. 24, 2008 (DE) ............... 10 2008 048 738

(51) Int. Cl.
*G01K 1/00*    (2006.01)
(52) U.S. Cl.
USPC ............ 374/141; 15/56; 239/101; 239/569; 137/238; 137/246; 374/143
(58) Field of Classification Search
USPC .......... 374/141, 147, 148, 143, 16, 27, 42, 4, 374/5, 7, 57; 15/56, 59, 57, 70, 74, 15/104.096, 104.5, 320, 362, 368; 137/238, 246, 246.13, 247, 244, 237; 422/1; 239/103, 104, 101, 569
See application file for complete search history.

(56) References Cited

U.S. PATENT DOCUMENTS

| | | | | |
|---|---|---|---|---|
| 2,443,550 A | * | 6/1948 | Zwosta | 137/208 |
| 2,790,063 A | * | 4/1957 | Bok et al. | 239/13 |
| 3,053,247 A | * | 9/1962 | Bradshaw | 126/110 R |
| 3,069,094 A | * | 12/1962 | Haloski | 239/261 |
| 3,109,831 A | * | 11/1963 | Seiner | 526/65 |
| 3,382,584 A | * | 5/1968 | Blake | 34/292 |
| 3,584,965 A | * | 6/1971 | Chastanier | 401/2 |
| 3,596,516 A | * | 8/1971 | Haynes et al. | 374/42 |
| 3,653,794 A | * | 4/1972 | Shakiba | 431/208 |
| 3,782,074 A | * | 1/1974 | Gardenier | 95/13 |
| 4,383,645 A | * | 5/1983 | Figiel et al. | 239/13 |
| 4,542,993 A | * | 9/1985 | Mims et al. | 374/42 |
| 4,561,785 A | * | 12/1985 | Long et al. | 374/42 |
| 4,822,570 A | * | 4/1989 | Lerman et al. | 422/119 |
| 4,932,788 A | * | 6/1990 | Yeh | 374/35 |
| 5,154,513 A | * | 10/1992 | Beer | 374/147 |
| 5,548,958 A | * | 8/1996 | Lewis | 60/693 |
| 5,564,448 A | * | 10/1996 | Lincoln | 134/166 R |
| 5,750,966 A | * | 5/1998 | Ruozi | 219/692 |
| 5,752,411 A | * | 5/1998 | Harpster | 73/861.04 |

(Continued)

FOREIGN PATENT DOCUMENTS

| | | |
|---|---|---|
| DE | 830999 C | 2/1952 |
| DE | 1174638 B | 7/1964 |

(Continued)

OTHER PUBLICATIONS

European Search Report for EP 09 16 9194 dated Jan. 6, 2010.

(Continued)

*Primary Examiner* — Gail Verbitsky
(74) *Attorney, Agent, or Firm* — Marshall, Gerstein & Borun LLP

(57) ABSTRACT

Reliably and quickly acting device that can be cheaply employed for monitoring the flow of water vapor, having a water vapor line extending between a switching valve and a cross-section connection, in particular a nozzle, and a temperature sensor monitoring the temperature in the line.

17 Claims, 1 Drawing Sheet

(56) References Cited

U.S. PATENT DOCUMENTS

| | | | |
|---|---|---|---|
| 5,853,246 A * | 12/1998 | Lowder | 374/109 |
| 6,715,499 B2 | 4/2004 | Bartels et al. | |
| 6,960,321 B1 | 11/2005 | Ludwig | |
| 2002/0159915 A1 | 10/2002 | Zelina et al. | |
| 2003/0014949 A1 | 1/2003 | Wakabayashi et al. | |
| 2003/0047198 A1* | 3/2003 | Fargnoli | 134/22.18 |
| 2004/0237466 A1* | 12/2004 | Grossmann et al. | 53/167 |
| 2005/0098575 A1* | 5/2005 | Carhuff et al. | 221/150 R |
| 2006/0207262 A1* | 9/2006 | Firey | 60/784 |
| 2007/0193610 A1* | 8/2007 | Strothoff et al. | 134/166 R |
| 2007/0251459 A1* | 11/2007 | Fukushima et al. | 119/14.18 |
| 2009/0130268 A1 | 5/2009 | Euler et al. | |
| 2010/0154833 A1* | 6/2010 | Endo et al. | 134/26 |
| 2011/0073618 A1* | 3/2011 | Anderson et al. | 222/148 |
| 2012/0018030 A1* | 1/2012 | Laumer et al. | 141/1 |
| 2013/0125928 A1* | 5/2013 | Cull | 134/22.1 |

FOREIGN PATENT DOCUMENTS

| | | | |
|---|---|---|---|
| DE | 4427570 | A1 | 2/1996 |
| DE | 4435415 | A1 * | 4/1996 |
| DE | 102004015441 | A1 | 10/2005 |
| DE | 20321071 | U1 | 11/2005 |
| DE | 102006023764 | A1 | 11/2007 |
| EP | 1144016 | A1 | 10/2001 |
| EP | 1932770 | A1 | 6/2008 |
| GB | 1001328 | | 0/1911 |
| JP | 55110703 | A * | 8/1980 |
| JP | 07139842 | A * | 6/1995 |
| JP | 09095302 | A * | 4/1997 |
| JP | 11209119 | A * | 8/1999 |
| JP | 2004299723 | A * | 10/2004 |
| JP | 2004305001 | A * | 11/2004 |
| JP | 2005279648 | A | 10/2005 |
| JP | 006234203 | A * | 9/2006 |
| JP | 2007039084 | A * | 2/2007 |
| JP | 2010008044 | A * | 1/2010 |
| WO | WO-2004098800 | A1 | 11/2004 |

OTHER PUBLICATIONS

German Search Report for 10 2008 048 738.4, dated Mar. 24, 2010.

* cited by examiner

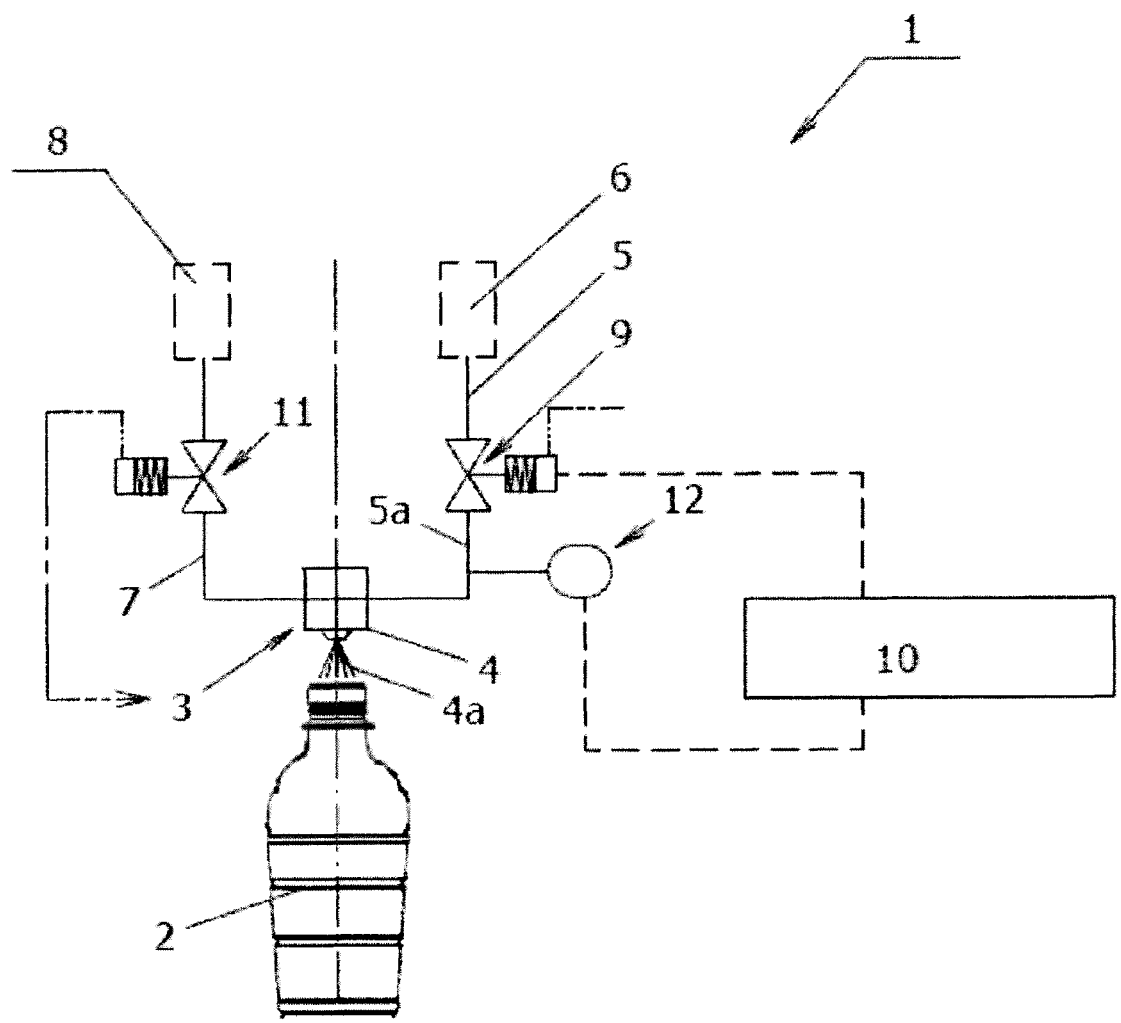

DEVICE FOR MONITORING THE FLOW OF WATER VAPOR

CROSS-REFERENCE TO RELATED APPLICATION

The present application claims the benefit of priority of German Patent Application No. 102008048738.4 filed Sep. 24, 2008. The entire text of the priority application is incorporated herein by reference in its entirety.

FIELD OF THE DISCLOSURE

The disclosure relates to a device and a method for monitoring the flow of water vapor.

BACKGROUND

Water vapor is employed in many applications, for example for cleaning and/or sterilizing or disinfecting containers for beverages. It is often necessary to ensure and document that the water vapor supplied with predetermined parameters, for example pressure and temperature, reaches the respective point with these predetermined parameters and has the desired effect at this point. For example, during the sterilization, disinfection and cleaning of containers for beverages, it has to be ensured that the desired effect is achieved at the treated objects, that means, for example, that the supplied water vapor with the predetermined temperature and/or the predetermined pressure also results in the desired heating of the container, but that the effect is not strong enough to cause any damage. This is, for example, particularly problematic if plastic bottles, for example PET bottles, are sterilized or disinfected with water vapor, as an unintended, stronger or longer heating very quickly leads to shrinkage or deformation of the plastics, thus making the containers useless. With these sensitive containers, a timed water vapor supply has proven of value, where the actual treatment duration is only extremely short and lasts, for example, from 0.5 to maximally 2 seconds.

In the past, many attempts have been made to develop devices which are intended to deter mine as quickly and precisely as required whether the treatment with water vapor has been sufficient.

For example, the DE 10 2006 023 764 describes a method and a device for sterilizing bottles or similar containers, where the temperature of the respective treated container is determined by at least one temperature sensor. This temperature must be determined at the end of the treatment section and at each container, so that errors are only recognized when the treatment is terminated, so that all containers that are being treated at this point in time must be rejected. The determination of the temperature is accomplished without contact by means of a pyrometer. While this method is very fast, it is susceptible to failures and very error-prone, in particular if the washing of the container is to be detected internally, while the container is simultaneously being washed with a fluid having the same or a similar temperature externally. In this situation, the temperature contrast is no longer sufficient for the pyrometer to detect the heat penetrating from the interior to the exterior of the container due to heat conduction. In case of an additional external washing process, the value that can be detected externally possibly greatly varies from the value at the inner surface.

Another device for monitoring the thermal treatment of bottles or the like is known from DE 44 27 570. This device contains a detector that can determine whether any sterilization fluid is present in the container by means of fluid measurement. To this end, a mist detector is employed which determines the density of the mist generated inside the container by the sterilization medium.

SUMMARY OF THE DISCLOSURE

The object underlying the disclosure is to provide a device and a method for monitoring the flow of water vapor that work quickly and reliably and can be employed at low costs.

The present disclosure deviates from the technique employed in prior art up to now of determining the conditions directly at the object to be treated, and it starts from the prerequisite that monitoring the flow of water vapor before the actual treatment procedure sufficiently reliably reflects the actual conditions and parameters of water vapor treatment, after a previous matching operation. Thereby, the present disclosure gets by with a relatively cheap temperature sensor, for example a thermoelement, which is arranged in the supply of the flow of water vapor itself, such that temperature and/or pressure changes can be easily detected under saturated vapor conditions. The disclosure can be employed for predicting a correct result of a treatment procedure of an object as well as for the correct functioning of a treatment device. Thus, for example in a treatment device for objects in which a plurality of objects are treated in a plurality of treatment sites one can determine whether one of the treatment sites does no longer work correctly, for example because its nozzle is clogged, by matching the temperature measured at each treatment site.

Advantageous further developments of the disclosure can be taken from the subclaims.

To create optimal conditions for the employment of the temperature sensor according to the disclosure, the dimensions of the measuring point should be carefully adjusted to create optimal conditions. This can be accomplished by changing a number of parameters.

The disclosure can be in particular employed in processes where the flow of water vapor is discontinuous, preferably timed, i.e. the treatment is accomplished by intermittent vapor blasts. In the process, the efficiency of the vapor blasts can be determined very quickly and at high precision by the monitoring temperature sensor by detecting the temperature reduction and its increase again to the predetermined value. But even in a continuous operation, one can, for example, determine by means of the disclosure whether one of the treatment sites among a plurality of treatment sites does not work correctly.

For implementing the disclosure as concerns the control technology, the thermoelements are read in directly at the valve control by means of analogue input modules. Depending on the switch conditions of one or several valves for the supply of a fluid, defined temperatures at defined points in time and/or defined periods are evaluated within a predetermined tolerance zone, and their dependencies are observed. If the values move within the predefined tolerance range, the treatment is rated to be successful. If these values are not achieved, an error message will be indicated in the visualization system. The container will be rejected before the subsequent treatment.

The physical effect of water vapor condensation at ambient temperature leads to a constant temperature being reached when the vapor supply is switched off, which temperature depends on the surrounding area, typically 100° C. at 1016 kPa. This physical interrelationship is used for matching and self-diagnosis of the measuring device in the controlling means.

BRIEF DESCRIPTION OF THE DRAWINGS

In the following, one embodiment of the disclosure is illustrated more in detail with reference to the single drawing.

FIG. 1 shows a device according to the disclosure for monitoring the flow of water vapor.

DETAILED DESCRIPTION

In the represented embodiment, the device 1 is shown in its preferred intended use in a disinfection system for containers, in particular containers for beverages 2, and it is particularly suited for cleaning and sterilizing beverage bottles of PET plastics. The disinfection system is of a conventional type and can be, for example, a sterilization system as it is described in the EP 1 144 016, where reference can be made to this citation for illustrating details.

The cleaning system shows a plurality of treatment sites 3 in which the containers 2 are treated with water vapor and possibly with an additional cleaning agent or disinfectant, for example peracetic acid or hydrogen peroxide or the like. Each treatment site 3 contains one or several nozzles 4 which spray the employed agents inside and/or outside onto the containers 2. The nozzle 4 is preferably embodied as combining nozzle which is in communication with a source of water vapor 6 via a first line 5 and with a source 8 for a cleaning agent or disinfectant via a second line 7 and discharges both agents in combination. The source of water vapor 6 and the source 8 for disinfectants can be provided together for a plurality of treatment sites 3 and be connected with the respective nozzles 4 at each treatment site 3 by means of suited distributors.

A switching valve 9 which is connected to an evaluation/control electronics 10 is provided in the water vapor line 5 and automatically activated by the same to supply water vapor from the source of water vapor 6 to the nozzle 4 discontinuously, preferably in a timed manner.

In the line 7 from the disinfection source 8 to the nozzle 4, too, an switching valve 11 is provided and also automatically activated and actuated by the evaluation/control electronics 10.

In a section 5a of the water vapor line 5 which extends downstream of the control valve 9 to the nozzle 4, a temperature sensor 12, preferably a thermoelement, for determining the temperature of the water vapor is provided. The temperature sensor 12, too, is connected to the evaluation/control electronics 10 for transmitting the data determined by the temperature sensor.

The water vapor line in the region of the section 5a and downstream of the connection of the temperature sensor 12 contains a reduction of the internal cross-section which is preferably formed by a reduced nozzle opening 4a, but can also be provided in the line 5a itself. By this reduction of the cross-section 4a, a back pressure of the saturated vapor is built in the region 5a of the water vapor line 5, the height of which can be precisely determined by means of the temperature measurement due to the fixed connection between the temperature and pressure of not superheated water vapor (steam table) by temperature measurement. The pressure head (matched with the switching times of the switching valve 9) is in turn a measure for the amount of water vapor employed per treatment procedure and thus for the intensity of the treatment procedure, in particular also with treatment times of between 0.5 to maximally 3 seconds. The back pressure in the line 5a should preferably correspond to the pressure of the supplied water vapor and be at least 0.5 bar overpressure, preferably between 2 to 4 bar overpressure.

To build up the back pressure, a cross-sectional ratio between the cross-section of line 5a and the cross-section of the reduction 4a within a range of between 40:1 and 5:1, preferably 10:1, has proven of value.

Here, the internal diameter of the line 5a can be between 2.0 mm and 10.0 mm, preferably between 2.0 mm and 8.0 mm, and in particular 4.0 mm. The internal diameter of the reduction 4a, in particular the nozzle 4, can be within a range of between 0.05 and 2 mm, preferably between 0.08 and 1.2 mm, and in particular 1 mm.

The volume of the line 5a between the switching valve 9 and the reduction 4a should be designed as small as possible in order not to unnecessarily prolongate the appearance of stable pressure conditions. Here, the smallest possible distance between the switching valve 9 and the reduction 4a can be just large enough for permitting the temperature sensor 12 to be installed. Lengths of up to 500 mm, preferably between 10 mm and 250 mm, and in particular 200 mm, are practicable.

The disclosure is in particular suited for monitoring a discontinuous, in particular a regularly timed, flow of water vapor, where by means of the temperature sensor 12 the rise and fall of the temperature and accordingly the rise and fall of the pressure can be determined in a very simple and quick way.

If the treatment system in which the device 1 according to the disclosure is employed contains several treatment sites 3, the values obtained from the individual temperature sensors 12 of the sites 3 can be compared to each other (in particular if all treatment sites are fed by the same source of water vapor 6), whereby one can very quickly and early detect if one of the treatment sites 3 does no longer work correctly, for example if the pressure in the line 5a is no longer reduced fast enough, as for example the nozzle 4 is getting clogged. This function can be also provided by the device according to the disclosure where a continuous flow of water vapor is employed.

In the operation of the device according to the disclosure, the control valves 9 and 11, controlled by the electronics 10, can be opened and closed at selected intervals in order to supply a non-superheated water vapor from the source of water vapor 6 and possibly a suited disinfectant 8 to the combining nozzle 4 at predetermined intervals. By the temperature sensor 12, here the saturated vapor temperature adjusted in the region 5a of the water vapor line 5 is detected, and the temperature drop is determined when the switching valve 9 is closed again. Measurement is effected directly without any essential delay in time during the treatment of the container 2. The values are transmitted to the electronics 10, stored therein and evaluated as well as possibly used for controlling the complete system or parts thereof.

If a plurality of treatment sites 3 is provided, a plausibility check of several treatment sites can be effected by matching, where it is assumed that each sensor must supply the same signal value in case of a perfect function of the device and the sensor when the steam pressure has the same effect everywhere. If this is not the case, one can intervene early and make corrections.

The disclosure is especially suited for monitoring intermittent flows of water vapor or gaseous fluids at a high enthalpy level and enthalpy change in case of a pressure change, which works the better the smaller the reduced cross-section is based on the line cross-section, and if the volume between the switching valve and the reduction is as small as possible.

In variation to the described and drawn embodiment, the reduction can also be provided within the line. The disclosure can be also employed for a mere water vapor treatment.

We claim:

1. A cleaning or disinfecting system for beverage containers comprising a device for monitoring a flow of water vapor, the monitoring device comprising a water vapor line extending between a switching valve and a portion with a reduction of a cross-section comprising a nozzle to spray the water vapor at least one of inside and outside onto the containers, and a temperature sensor downstream of the switching valve that monitors the temperature in the water vapor line.

2. Device according to claim 1, wherein the temperature sensor is a thermoelement.

3. Device according to claim 1, wherein the cross-section of the portion with the reduction of the cross-section is dimensioned-to build up a back pressure-in the water vapor line-between approximately 2 and 4 bar overpressure.

4. Device according to claim 1, wherein a cross-sectional ratio between a cross-section of the water vapor line and the cross-section of the portion with the reduction of the cross-section is within a range of between approximately 40:1 and 5:1.

5. Device according to claim 1, wherein an internal diameter of the water vapor line is between approximately 2.0 mm and 10.0 mm.

6. Device according to claim 1, wherein an internal diameter of the portion with the reduction of the cross-section is within a range of approximately 0.05 mm and 2 mm.

7. Device according to claim 1, wherein the flow of water vapor is discontinuous.

8. Device according to claim 1, wherein the device is disposed in a cleaning or disinfecting system for beverage containers-where the reduction is formed by a combined nozzle which is connected to a source of water vapor via the water vapor line and to a source for a cleaning/sterilization agent via another line.

9. Device according to claim 4, wherein the cross-sectional ratio is approximately 10:1.

10. Device according to claim 5, wherein the initial diameter is between approximately 2.0 mm and 8.0 mm.

11. Device according to claim 6, wherein the internal diameter is approximately 4.0 mm.

12. Device according to claim 6, wherein the internal diameter is between approximately 0.08 mm and 1.2 mm.

13. Device according to claim 6 wherein the internal diameter is approximately 1 mm.

14. Method of monitoring the flow of water vapor in a cleaning or disinfecting system for beverage containers comprising a water vapor line extending between a switching valve and a portion with a reduction of a cross section comprising a nozzle to spray the water vapor at least one of inside and outside onto the containers, the method comprising monitoring the temperature of the flow of water vapor between the switching valve and the reduction of the cross-section.

15. Method according to claim 14, and building a back pressure between the switching valve and the reduction.

16. Method according to claim 14, wherein the flow of water vapor is discontinuous.

17. A cleaning or disinfecting system for beverage containers comprising a device for monitoring a flow of water vapor, the monitoring device comprising a water vapor line extending between a switching valve and a portion with a reduction of a cross-section comprising a nozzle to spray the water vapor at least one of inside and outside onto the containers, and a temperature sensor downstream of the switching valve that monitors the temperature in the water vapor line, wherein the temperature sensor and the switching valve are connected to a control electronics and the switching valve is actuated by the control electronics in a timed manner.

* * * * *